United States Patent
Heo et al.

(10) Patent No.: US 11,291,848 B2
(45) Date of Patent: Apr. 5, 2022

(54) METHOD FOR SUPPLYING POWER TO IMPLANTABLE MEDICAL DEVICE AND POWER SUPPLY SYSTEM USING THE SAME

(71) Applicants: SAMSUNG ELECTRONICS CO., LTD., Suwon-si (KR); SAMSUNG LIFE PUBLIC WELFARE FOUNDATION, Seoul (KR)

(72) Inventors: Manseung Heo, Seoul (KR); Jinho Oh, Seoul (KR); Eunkyoung Park, Seoul (KR); Minyoung Lee, Seoul (KR); Kyusung Lee, Seoul (KR)

(73) Assignees: Samsung Electronics Co., Ltd., Suwon-si (KR); Samsung Life Public Welfare Foundation, Seoul (KR)

( * ) Notice: Subject to any disclaimer, the term of this patent is extended or adjusted under 35 U.S.C. 154(b) by 358 days.

(21) Appl. No.: 16/087,939

(22) PCT Filed: Jun. 15, 2016

(86) PCT No.: PCT/KR2016/006356
§ 371 (c)(1),
(2) Date: Sep. 24, 2018

(87) PCT Pub. No.: WO2017/164460
PCT Pub. Date: Sep. 28, 2017

(65) Prior Publication Data
US 2020/0269056 A1    Aug. 27, 2020

(30) Foreign Application Priority Data
Mar. 22, 2016  (KR) .................. 10-2016-0034069

(51) Int. Cl.
*A61N 1/378* (2006.01)
*H02J 50/10* (2016.01)
(Continued)

(52) U.S. Cl.
CPC ......... *A61N 1/3787* (2013.01); *A61N 1/3785* (2013.01); *H02J 7/02* (2013.01);
(Continued)

(58) Field of Classification Search
CPC ..... A61N 1/3787; A61N 1/3785; H02J 50/10; H02J 50/70; H02J 7/02
See application file for complete search history.

(56) References Cited

U.S. PATENT DOCUMENTS 7,650,186 B2 * 1/2010 Hastings ............ A61N 1/37223
607/32
8,766,482 B2 7/2014 Cook et al.
(Continued)

FOREIGN PATENT DOCUMENTS

| KR | 10-2011-0029449 A | 3/2011 |
|----|---|---|
| KR | 10-2014-0105043 A | 9/2014 |
| KR | 10-2015-0108939 A | 9/2015 |

OTHER PUBLICATIONS

Extended European Search Report dated Aug. 26, 2019 in corresponding European Patent Application No. 16895586.2 (9pages in English).
(Continued)

*Primary Examiner* — Daniel Cavallari
*Assistant Examiner* — Brian K Baxter
(74) *Attorney, Agent, or Firm* — NSIP Law

(57) ABSTRACT

Provided are a method for supplying power to an implantable medical device and a power supply system for an implantable medical device. The power supply system supplies a constant power to the implantable medical device even when there is a movement in a body, by using a wireless power transmitter unit, a wireless power receiver unit, and a piezoelectric sensor unit stacked at the wireless power receiver unit.

18 Claims, 13 Drawing Sheets

(51) Int. Cl.
    *H02J 50/70*           (2016.01)
    *H02J 7/02*            (2016.01)

(52) U.S. Cl.
    CPC .............. *H02J 50/10* (2016.02); *H02J 50/70* (2016.02); *H02J 2207/20* (2020.01)

(56) References Cited

U.S. PATENT DOCUMENTS

| | | | |
|---|---|---|---|
| 8,777,863 B2 | 7/2014 | Piaget et al. | |
| 8,825,161 B1* | 9/2014 | Mi | A61N 1/37217 607/37 |
| 8,829,731 B2 | 9/2014 | Baarman et al. | |
| 8,872,507 B2* | 10/2014 | Niessen | H01M 10/44 324/205 |
| 9,554,411 B1* | 1/2017 | Hall | A61N 1/3787 |
| 9,847,739 B2 | 12/2017 | Deterre et al. | |
| 2004/0046483 A1 | 3/2004 | Dupont et al. | |
| 2007/0282378 A1* | 12/2007 | Huang | A61N 1/3787 607/2 |
| 2008/0214132 A1* | 9/2008 | Kurokawa | G06K 19/0723 455/272 |
| 2009/0062886 A1* | 3/2009 | O'Handley | G01R 33/18 607/51 |
| 2009/0121585 A1* | 5/2009 | Lee | H01M 10/0565 310/319 |
| 2010/0114142 A1 | 5/2010 | Albrecht et al. | |
| 2010/0317978 A1 | 12/2010 | Maile et al. | |
| 2011/0190852 A1 | 8/2011 | Dinsmoor et al. | |
| 2011/0196192 A1 | 8/2011 | Forsell | |
| 2011/0201870 A1 | 8/2011 | Forsell | |
| 2011/0218594 A1* | 9/2011 | Doron | H04B 11/00 607/60 |
| 2011/0295241 A1* | 12/2011 | Ziaie | A61N 1/32 604/890.1 |
| 2012/0055257 A1* | 3/2012 | Shaw-Klein | H01L 41/1132 73/780 |
| 2012/0187772 A1 | 7/2012 | Teggatz et al. | |
| 2014/0155959 A1 | 6/2014 | Forsell | |
| 2015/0365018 A1 | 12/2015 | Inman et al. | |
| 2015/0372513 A1* | 12/2015 | Choi | H02J 7/0013 320/125 |
| 2016/0000548 A1* | 1/2016 | Aiden | A61F 4/00 623/23.72 |
| 2016/0045184 A1* | 2/2016 | Courtney | A61B 8/483 600/424 |
| 2017/0046687 A1* | 2/2017 | Stern | G06Q 20/355 |
| 2017/0271919 A1* | 9/2017 | Von Novak, III | H02J 50/10 |
| 2017/0338670 A1* | 11/2017 | Zhang | H02J 7/00714 |
| 2018/0085593 A1* | 3/2018 | Fayram | H02J 50/80 |
| 2019/0044380 A1* | 2/2019 | Lausch | A61N 1/3787 |
| 2019/0252904 A1* | 8/2019 | Tian | H02J 7/02 |

OTHER PUBLICATIONS

Korean Office Action dated Dec. 13, 2018 in corresponding Korean Patent Application No. 10-2016-0034069 (4 pages in English and 5 pages in Korean).

International Search Report dated Nov. 21, 2016 in counterpart International Patent Application No. PCT/KR2016/006356.

* cited by examiner

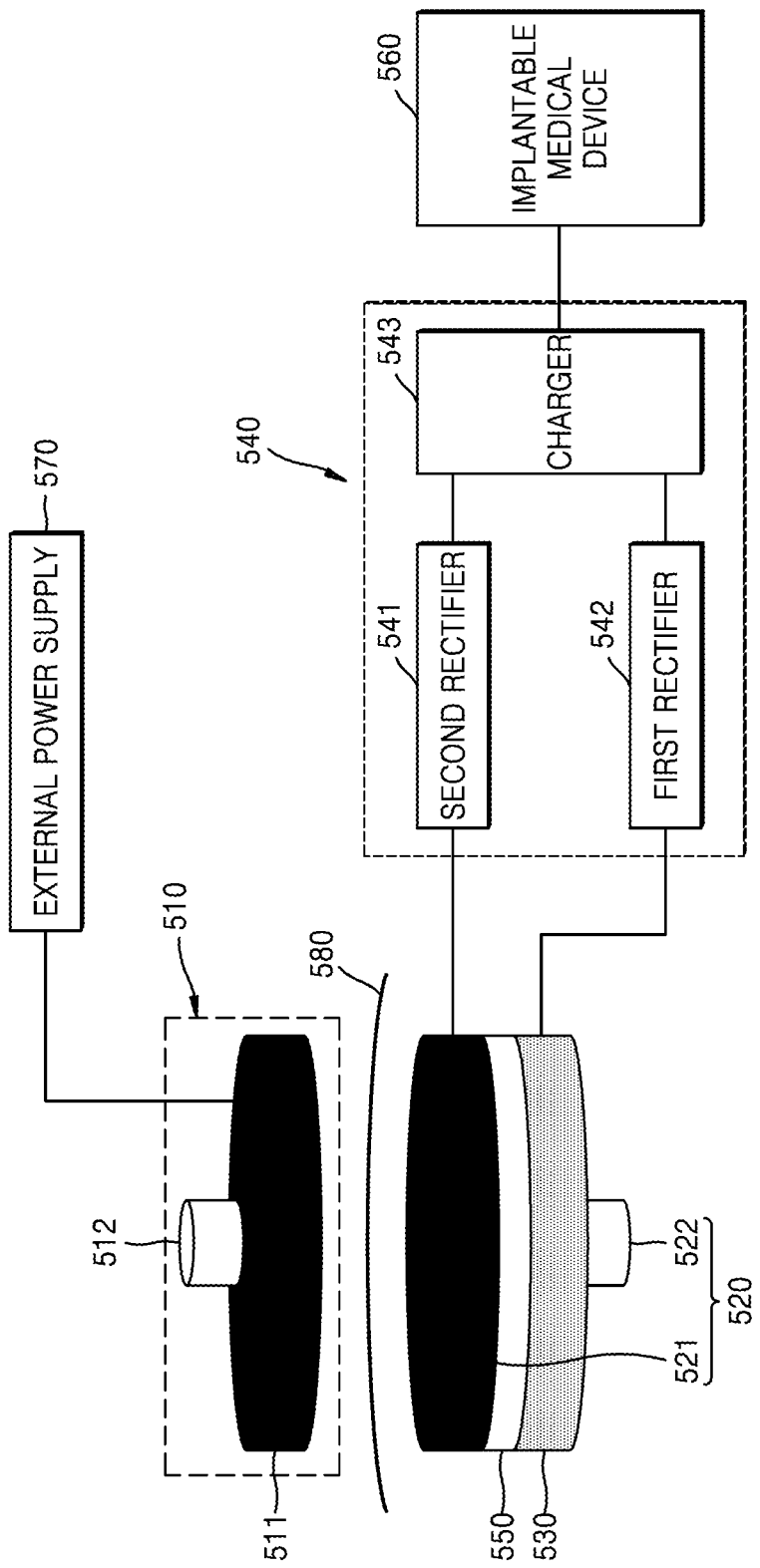

METHOD FOR SUPPLYING POWER TO IMPLANTABLE MEDICAL DEVICE AND POWER SUPPLY SYSTEM USING THE SAME

CROSS REFERENCE TO RELATED APPLICATION(S)

This application is a U.S. National Stage Application of International Application No. PCT/KR2016/006356, filed on Jun. 15, 2016, which claims the benefit of Korean Patent Application No. 10-2016-0034069, filed on Mar. 22, 2016, in the Korean Intellectual Property Office, the entire disclosures of which are incorporated by reference for all purposes.

TECHNICAL FIELD

The present disclosure relates to methods for supplying power to an implantable medical device and power supply systems using the same.

BACKGROUND ART

Implantable medical devices refer to medical devices implanted into human bodies, and have recently been used for diagnosis and treatment of diseases. For example, the implantable medical devices may include pacemakers, implantable cardioverter defibrillators (ICDs), neurostimulators, and deep brain stimulation systems used for deep brain stimulation (DBS). The implantable medical devices may be implanted into human bodies for a long time to sense diseases or alleviate the symptoms of diseases.

In order for an implantable medical device to operate in a body, power should be continuously supplied to the implantable medical device. Accordingly, research has been conducted on a power supply system for the implantable medical device.

DESCRIPTION OF EMBODIMENTS

Technical Problem

Provided are methods for supplying power to implantable medical devices and power supply systems for implantable medical devices. The technical solutions to be achieved by the present embodiment are not limited to the above technical solutions, and other technical solutions may be derived from the following embodiments.

Solution to Problem

According to an aspect of the present disclosure, a power supply system for an implantable medical device includes: a wireless power transmitter unit located outside a body to generate a magnetic field when a first alternating current (AC) is applied thereto; a wireless power receiver unit located inside the body to generate a second alternating current by the magnetic field generated by the wireless power transmitter unit; and a piezoelectric sensor unit stacked at the wireless power receiver unit to generate a voltage according to a pressure applied thereto.

The wireless power receiver unit and the piezoelectric sensor unit may have a flexible form.

The form of the piezoelectric sensor unit stacked at the wireless power receiver unit may be modified according as the form of the wireless power receiver unit is modified due to a pressure applied thereto as the body moves; and the piezoelectric sensor unit may generate a voltage due to the modification.

The power supply system may further include a shield unit located between the wireless power receiver unit and the piezoelectric sensor unit to shield the second alternating current.

The wireless power receiver unit may include: a coil configured to generate the second alternating current; and a magnet configured to fix the coil.

The piezoelectric sensor unit may be located between the coil and the magnet.

The power supply system may further include a charger unit configured to charge a voltage output from the wireless power receiver unit and a voltage output from the piezoelectric sensor unit.

The charger unit may include: a first rectifier configured to convert a voltage output from the piezoelectric sensor unit into a first direct current (DC) voltage; a second rectifier configured to convert a second AC voltage corresponding to the second alternating current output from the wireless power receiver unit into a second DC voltage; and a capacitor configured to charge the first DC voltage and the second DC voltage.

The charger unit may transmit a constant power to the implantable medical device.

The wireless power receiver unit may be located at a subcutaneous fat of the body.

According to another aspect of the present disclosure, a method for supplying power to an implantable medical device includes: generating a magnetic field when a first alternating current (AC) is applied to a wireless power transmitter unit located outside a body; generating a second alternating current by the generated magnetic field by a wireless power receiver unit located inside the body; and generating a voltage based on an applied pressure by a piezoelectric sensor unit stacked at the wireless power receiver unit.

The wireless power receiver unit and the piezoelectric sensor unit may have a flexible form.

The form of the piezoelectric sensor unit stacked at the wireless power receiver unit may be modified according as the form of the wireless power receiver unit is modified due to a pressure applied thereto as the body moves; and the piezoelectric sensor unit may generate a voltage due to the modification.

The second alternating current may be shielded by a shield unit.

The wireless power receiver unit may include: a coil configured to generate the second alternating current; and a magnet configured to fix the coil.

The piezoelectric sensor unit may be located between the coil and the magnet.

The method may further include charging a voltage output from the wireless power receiver unit and a voltage output from the piezoelectric sensor unit.

The charging may include: converting a voltage output from the piezoelectric sensor unit into a first direct current (DC) voltage; converting a second AC voltage corresponding to the second alternating current output from the wireless power receiver unit into a second DC voltage; and charging the first DC voltage and the second DC voltage.

The method may further include supplying a constant power to the implantable medical device by using the charged voltage.

The wireless power receiver unit may be located at a subcutaneous fat of the body.

Advantageous Effects of Disclosure

As described above, since the wireless power supply based on the magnetic induction and the power supply based on the piezoelectric effect may be performed, a constant power may be supplied to the implantable medical device even when there is a movement in the body.

BRIEF DESCRIPTION OF DRAWINGS

FIG. 5 is a diagram illustrating a power supply system according to an embodiment.

MODE OF DISCLOSURE

Figure 1A:
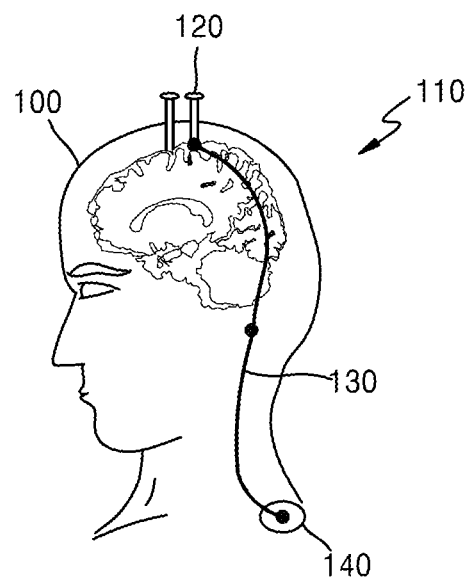
FIG. 1A is a diagram illustrating a deep brain stimulation system.

As the terms used herein, so far as possible, widely-used general terms are selected in consideration of functions in the embodiments; however, these terms may vary according to the intentions of those skilled in the art, the precedents, or the appearance of new technology. Also, in some cases, there may be terms that are optionally selected, and the meanings thereof will be described in detail in the corresponding portions of the description of the embodiment. Therefore, the terms used herein are not simple terms and should be defined based on the meanings thereof and the overall description of the embodiments.

In the descriptions of the embodiments, when an element is referred to as being "connected" to another element, it may be "directly connected" to the other element or may be "electrically connected" to the other element with one or more intervening elements therebetween. Also, when something is referred to as "including" a component, another component may be further included unless specified otherwise. Also, as used herein, the terms "units" and "modules" may refer to units that perform at least one function or operation, and the units may be implemented as hardware or software or a combination of hardware and software.

Although terms such as "first" and "second" may be used herein to describe various elements or components, the elements or components should not be limited by the terms. These terms are only used to distinguish one element or component from another element or component.

Also, connection members or connection lines between elements illustrated in the drawings merely represent examples of physical or logical connections and/or functional connections. In actual devices, the connection between elements may be represented by various alternative or additional functional connections, physical connections, or logical connections.

The term such as "comprise" or "include" used herein should not be construed as necessarily including all of the elements or operations (or steps) described herein, and should be construed as not including some of the described elements or operations (or steps) or as further including additional elements or operations (or steps).

The following description of embodiments should not be construed as limiting the scope of the present disclosure, and those that may be easily inferred by those of ordinary skill in the art should be construed as being included in the scope of the embodiments. Hereinafter, embodiments will be described in detail merely as examples with reference to the accompanying drawings.

Figure 1B:
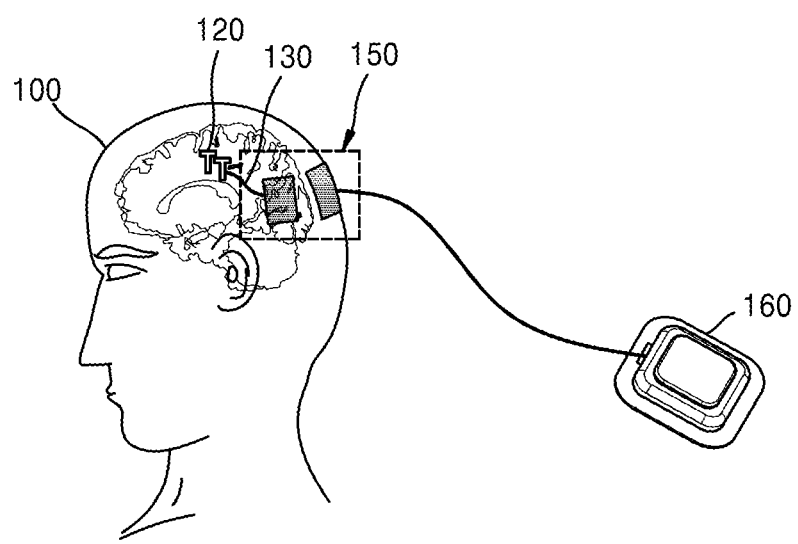
FIG. 1B is a diagram illustrating a deep brain stimulation system and a power supply system according to an embodiment.

FIGS. 1A and 1B are diagrams illustrating an implantable medical device and a power supply system according to an embodiment.

The implantable medical device may refer to a medical device implanted into a human body. Referring to FIGS. 1A and 1B, a deep brain stimulation system 110 used for deep brain stimulation (DBS) may be an implantable medical device that is implanted into a brain of a patient 100 to transmit an electrical stimulus to a certain part of the brain. For example, the deep brain stimulation may be used to treat chronic pain, Parkinson's disease, and dystonia.

FIG. 1A is a diagram illustrating a deep brain stimulation system.

Referring to FIG. 1A, the deep brain stimulation system 110 may include a lead 120, an extension 130, and an implanted pulse generator (IPG) 140.

The lead 120 may include a thin insulated line and a plurality of electrodes. The lead 120 may be located at a focus and may be connected to the implanted pulse generator 140 through the extension 130. Also, the lead 120 may transmit an electrical stimulus output from the implanted pulse generator 140 to a brain part where a neural activity is disturbed.

The implanted pulse generator 140 may generate a micro electrical stimulus and transmit the same to the lead 120, and may include a battery to generate an electrical stimulus. The implanted pulse generator 140 including the battery may be implanted into a subcutaneous collarbone or an abdomen due to safety and volume. That is, since the implanted pulse generator 140 including the battery has a larger volume than the lead 120, it may be implanted near the focus. In the case of the implanted pulse generator 140 including the battery, a surgical procedure may need to be performed to periodically replace the battery in consideration of the battery life. In general, the implanted pulse generator 140 including the battery may have an average replacement period of about five years. Thus, since the implanted pulse generator 140 including the battery has a large volume and should be periodically replaced, it may increase a burden on the patient 100.

FIG. 1B is a diagram illustrating a deep brain stimulation system and a power supply system according to an embodiment.

Referring to FIG. 1B, on behalf of the implanted pulse generator 140, a power supply system 150 may generate an electrical stimulus and transmit the same to the lead 120. In this case, the power supply system 150 may be implanted into a subcutaneous fat adjacent to the lead 120 to receive the power from an external power supply 160 and supply the same to the lead 120. The power supply system 150 may replace the battery included in the implanted pulse generator 140 of FIG. 1A, thus maintaining a small size. Also, the power supply system 150 may be semipermanently used and thus does not need to be periodically replaced.

Figure 2A:
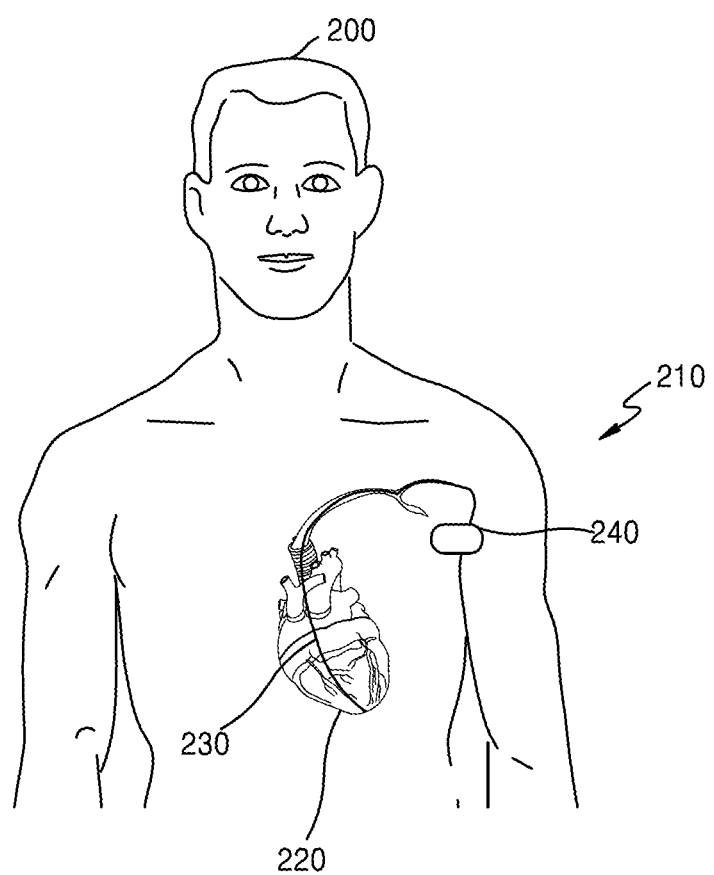
FIG. 2A is a diagram illustrating a pacemaker.
Figure 2B:
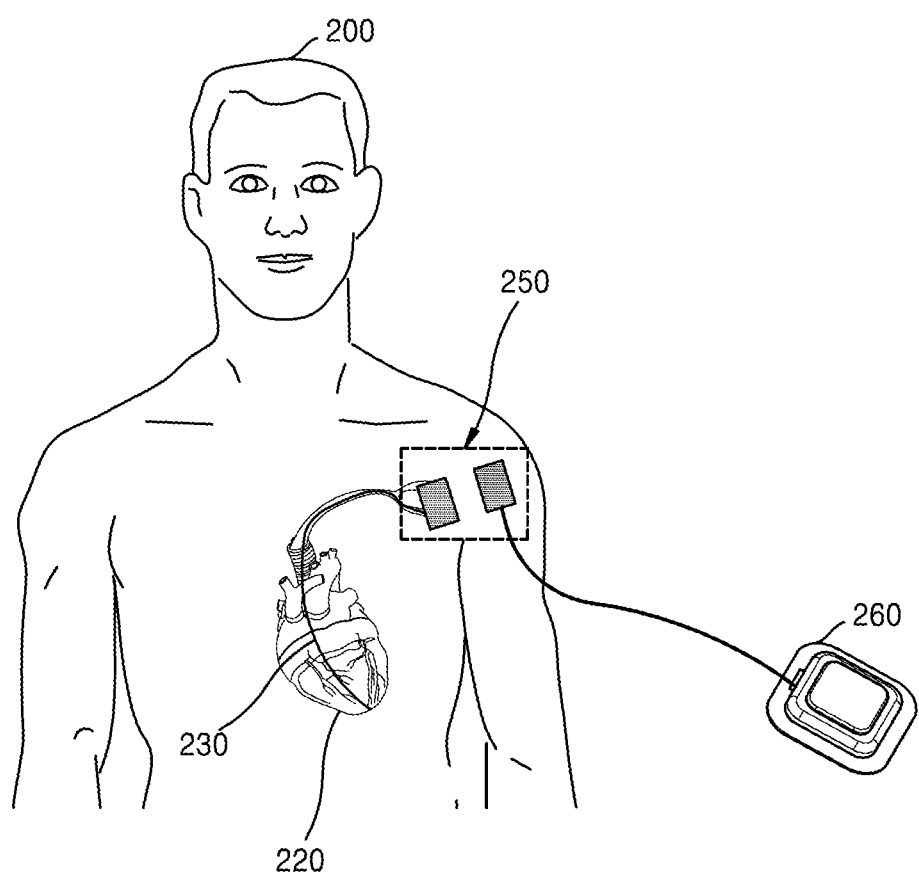
FIG. 2B is a diagram illustrating a pacemaker and a power supply system according to an embodiment.

FIGS. 2A and 2B are diagrams illustrating an implantable medical device and a power supply system according to another embodiment.

The power supply system may be applied to any implantable medical device. For example, the power supply system may be used to supply power to a pacemaker.

FIG. 2A is a diagram illustrating a pacemaker.

Referring to FIG. 2A, a pacemaker 210 may be an implantable medical device that is used to treat cardiac heart failure and bradyarrhythmia caused by a slow pulse. The pacemaker 210 may include an electrode 220, an extension 230, and a pulse generator 240.

The electrode 220 may be implanted into a heart muscle of a patient 200 to sense an electrical signal from a heart and transmit an electrical stimulus to the heart in the case of a slow pulse. Also, the electrode 220 may be connected to the pulse generator 240 through the extension 230.

The pulse generator 240 may generate an electrical stimulus and transmit the same to the electrode 220. The pulse generator 240 may include a battery to generate an electrical stimulus. In this case, the pulse generator 240 may be implanted into a collarbone part due to the problem of the stability and volume of the battery. Also, the pulse generator 240 should be periodically replaced because the battery life is limited.

FIG. 2B is a diagram illustrating a pacemaker and a power supply system according to an embodiment.

Referring to FIG. 2B, on behalf of the pulse generator 240, a power supply system 250 may transmit an electrical stimulus to the electrode 220 of the pacemaker 210.

Since the power supply system 250 has a smaller volume than the battery, it may be implanted into a subcutaneous fat adjacent to the electrode 220. Also, in the case of an implantable medical device receiving an electrical stimulus through the power supply system 250, it may be semipermanently used.

In addition to the deep brain stimulation system of FIG. 1B and the pacemaker of FIG. 2B, the power supply system may be used in an implantable medical device including an implantable cardioverter defibrillator (ICD), a neurostimulator, a gastric stimulator, and a foot drop implant.

Figure 3:
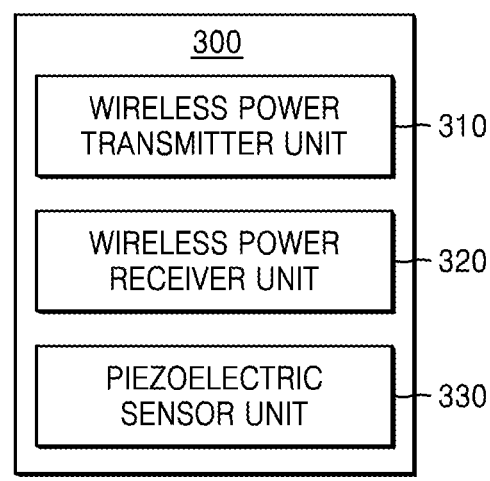
FIG. 3 is a block diagram illustrating a power supply system according to an embodiment.

FIG. 3 is a block diagram illustrating a power supply system according to an embodiment.

Referring to FIG. 3, a power supply system 300 may include a wireless power transmitter unit 310, a wireless power receiver unit 320, and a piezoelectric sensor unit 330.

The power supply system 300 may be defined as a system that may be partially implanted into a body to supply power to an implantable medical device.

The wireless power transmitter unit 310 may be located outside the body to generate a magnetic field when a first alternating current (AC) is applied thereto. The wireless power transmitter unit 310 may include a coil through which an alternating current may flow and a magnet that may fix the coil. When an alternating current flows through the coil of the wireless power transmitter unit 310, a magnetic field is generated around the coil according to the magnetic induction principle. In this case, when the magnetic field generated by the wireless power transmitter unit 310 reaches the wireless power receiver unit 320, a magnetic field is generated by the wireless power receiver unit 320 and a second alternating current is generated due to the magnetic field generated by the wireless power receiver unit 320, thus making it possible to provide wireless power supply.

The wireless power transmitter unit 310 may have the form of a cylindrical shape (cage) including a magnet and a coil, and may be configured to supply power when the body or a portion of the body is located in the cylindrical shape. Also, the wireless power transmitter unit 310 may be a portable device including a magnet and a coil, and may be configured to supply power when it approaches the implantation position of the wireless power receiver unit 320. However, the form of the wireless power transmitter unit 310 is not limited thereto.

The wireless power receiver unit 320 may be located inside the body to generate a second alternating current by the magnetic field generated by the wireless power transmitter unit 310. Specifically, the wireless power receiver unit 320 may be located at a subcutaneous fat of the body; however, the position of the wireless power receiver unit 320 is not limited thereto if only the wireless power receiver unit 320 is located within a region influenced by the magnetic field of the wireless power transmitter unit 310. Also, the wireless power receiver unit 320 may include a coil through which the second alternating current flows and a magnet that is configured to fix the coil. Also, the form of the wireless power receiver unit 320 may be modified.

The piezoelectric sensor unit 330 may include a sensor having a thin piezoelectric element inserted between metal plates and may generate a voltage by using the piezoelectric effect.

The piezoelectric sensor unit 330 may be stacked at the wireless power receiver unit 320 to generate a voltage according to a pressure applied thereto. Also, the piezoelectric sensor unit 330 may be located between the magnet and the coil of the wireless power receiver unit 320.

Also, the form of the piezoelectric sensor unit 330 may be modified. The form of the piezoelectric sensor unit 330 may be modified according to a pressure applied thereto as the body moves, and the piezoelectric sensor unit 330 may generate a voltage due to the modification.

Figure 4:
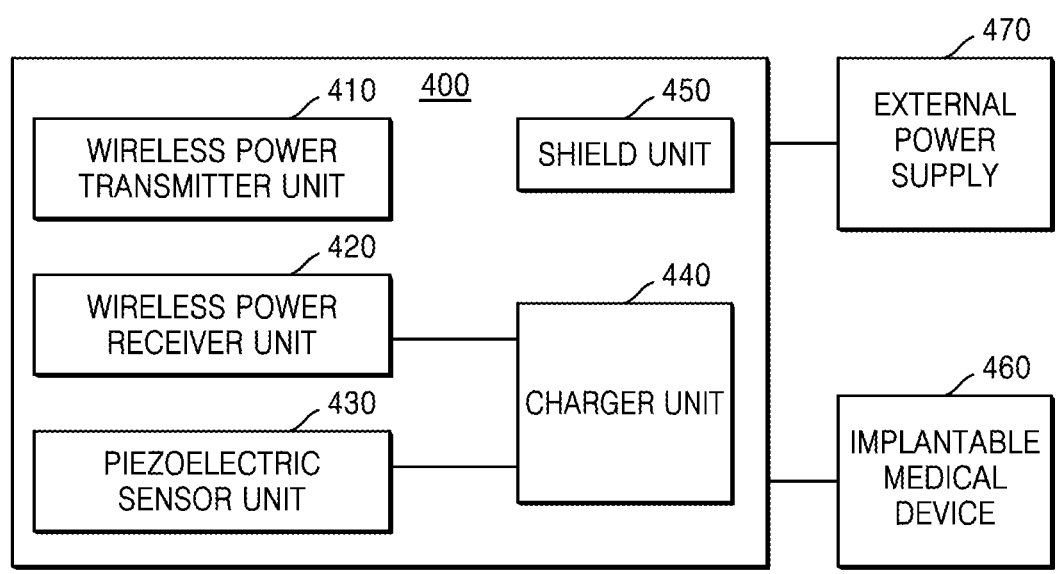
FIG. 4 is a detailed block diagram illustrating a power supply system according to another embodiment.

FIG. 4 is a detailed block diagram illustrating a power supply system according to another embodiment.

Referring to FIG. 4, a power supply system 400 may include a wireless power transmitter unit 410, a wireless power receiver unit 420, a piezoelectric sensor unit 430, a charger unit 440, and a shield unit 450.

The wireless power transmitter unit 410, the wireless power receiver unit 420, and the piezoelectric sensor unit 430 may correspond to the wireless power transmitter unit 310, the wireless power receiver unit 320, and the piezoelectric sensor unit 330 of FIG. 3, and thus detailed descriptions thereof will be omitted herein.

The charger unit 440 may convert a voltage output from the piezoelectric sensor unit 430 and an alternating current (AC) voltage corresponding to a second alternating current output from the wireless power receiver unit 420 respectively into a first direct current (DC) voltage and a second DC voltage, and may charge the first and second DC voltages. Also, the charger unit 440 may transmit a constant power to an implantable medical device 460 by using the charged voltage.

The shield unit 450 may be stacked between the piezoelectric sensor unit 430 and the coil of the wireless power receiver unit 420 to shield the second alternating current generated by the wireless power receiver unit 420. Also, the charger unit 450 may shield the generated current such that the voltage generated by the piezoelectric sensor unit 430 does not influence the wireless power receiver unit 420.

The power supply system 400 may be connected to the implantable medical device 460 and an external power supply 470.

The implantable medical device 460 may be defined as a device that may be implanted into a body to sense and treat a disease. For example, it may be, but is not limited to, a lead of a deep brain stimulation system or an electrode of a pacemaker. The implantable medical device 460 may receive an electrical stimulus or power from the power supply system 400.

The external power supply 470 may be connected to the wireless power transmitter unit 410 to transmit an alternating current to the wireless power transmitter unit 410.

FIG. 5 is a diagram illustrating a power supply system according to an embodiment.

Referring to FIG. 5, in a power supply system 500, with respect to a skin 580 of a body, a wireless power transmitter unit 510 may be located outside the body, and a wireless power receiver unit 520 and a piezoelectric sensor unit 530 may be located inside the body. For example, the wireless power receiver unit 520 and the piezoelectric sensor unit 530 may be located at a subcutaneous fat of the body. However, the position of the wireless power receiver unit 520 is not limited thereto if only the wireless power receiver unit 520 is located inside a magnetic field region of the wireless power transmitter unit 510.

The wireless power transmitter unit 510 may include a coil 511 and a magnet 512, and the wireless power receiver unit 520 may include a coil 521 and a magnet 522. Also, a shield unit 550 and the piezoelectric sensor unit 530 may be located between the coil 521 and the magnet 522 of the wireless power receiver unit 520. The shield unit 550 may shield a current generated by the coil 521 of the wireless power receiver unit 520, so that the piezoelectric sensor unit 530 is not influenced by the current generated by the coil 521 of the wireless power receiver unit 520.

Also, when the angle and distance between the wireless power transmitter unit 510 and the wireless power receiver unit 520 changes, the loss of power generated in the wireless power receiver unit 520 may increase. Thus, the piezoelectric sensor unit 530 may be stacked at the wireless power receiver unit 520 such that the loss of wireless power caused by a movement in the body may be compensated for.

In this case, when a first alternating current is applied from an external power supply 570 to the coil 511 of the wireless power transmitter unit 510, a magnetic field may be generated by the wireless power transmitter unit 510. When the magnetic field is generated, a second alternating current may be generated by the coil 521 of the wireless power receiver unit 520 according to the magnetic induction principle.

The piezoelectric sensor unit 530 may generate a voltage by a pressure applied inside the body, for example, by a pressure applied to the piezoelectric sensor unit 530 due to a body movement.

Also, the voltage corresponding to the second alternating current generated by the wireless power receiver unit 520 and the voltage generated by the piezoelectric sensor unit 530 may be input to the charger unit 540.

The charger unit 540 may include a first rectifier 542, a second rectifier 541, and a charger 543. The first rectifier 542 may be connected to the piezoelectric sensor unit 530 to convert the voltage generated by the piezoelectric sensor unit 530 into a first DC voltage. The second rectifier 541 may be connected to the coil 521 of the wireless power receiver unit 520 to convert the voltage corresponding to the second alternating current generated by the coil 521 of the wireless power receiver unit 520 into a second DC voltage. The charger 543 may be connected to the first rectifier 542 and the second rectifier 541 to charge the DC voltage output from the first rectifier 542 and the second rectifier 541. Also, the charger 543 may transmit the charged DC voltage to an implantable medical device 560. In this case, since the charger 543 may transmit a constant power to the implantable medical device 560, the implantable medical device 560 may operate stably.

Figure 6A:
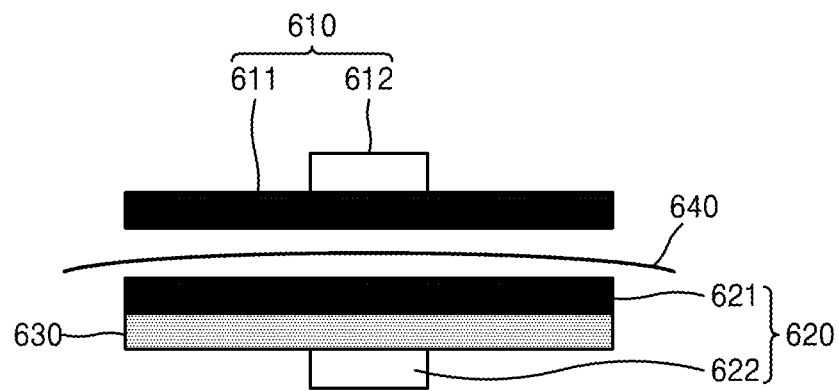
FIG. 6A is a diagram illustrating a power supply system according to an embodiment when there is no movement in a body.
Figure 6B:
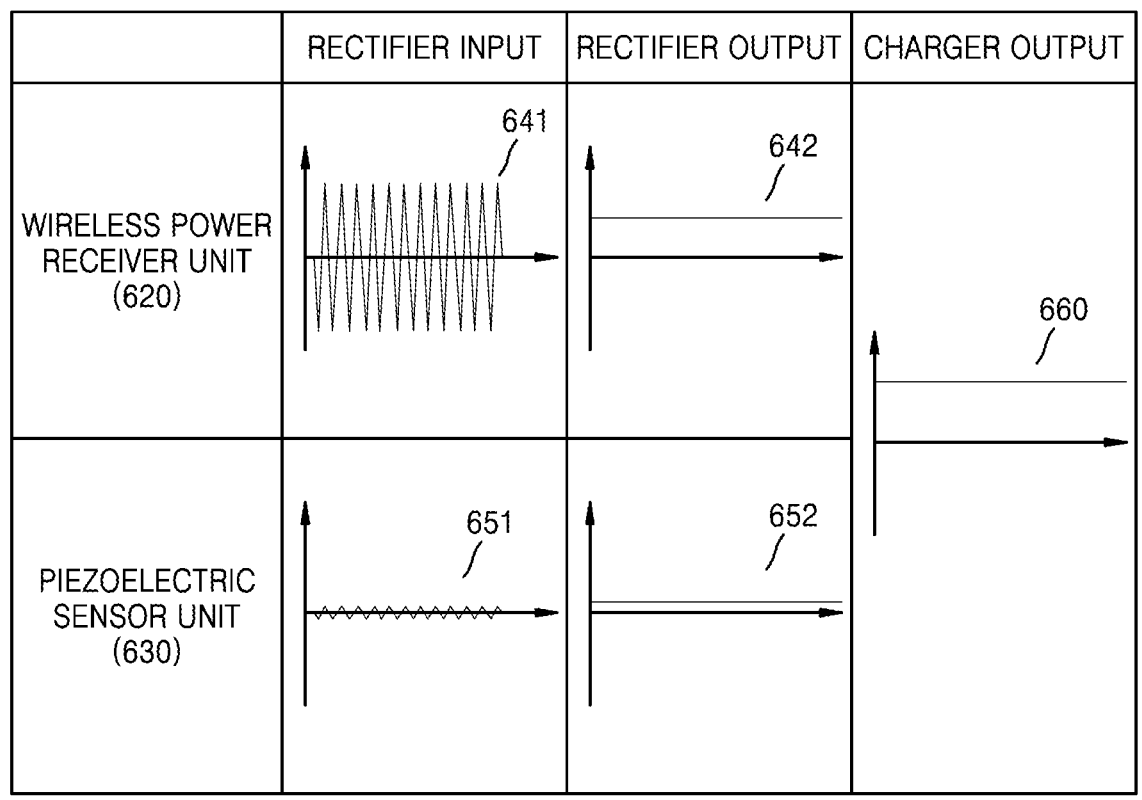
FIG. 6B is graphs illustrating voltages generated by a wireless power receiver unit and a piezoelectric sensor unit of a power supply system according to an embodiment when there is no movement in a body.

FIGS. 6A and 6B are diagrams illustrating voltages generated by a wireless power receiver unit and a piezoelectric sensor unit of a power supply system according to an embodiment when there is no movement in a body.

FIG. 6A is a diagram illustrating a power supply system according to an embodiment when there is no movement in a body.

Referring to FIG. 6A, a wireless power transmitter unit 610 may include a coil 611 and a magnet 612. A wireless power receiver unit 620 may be implanted inside a skin 640 and may include a coil 621 and a magnet 622. Also, a piezoelectric sensor unit 630 may be stacked at the coil 621 of the wireless power receiver unit 620 and may be located between the coil 621 and the magnet 622. The magnet 622 may be configured to fix the coil 621 and the piezoelectric sensor unit 630.

FIG. 6B is graphs illustrating voltages generated by a wireless power receiver unit and a piezoelectric sensor unit of a power supply system according to an embodiment when there is no movement in a body.

When there is no movement in the body, the wireless power receiver unit 620 may generate a second alternating current having a similar amplitude to a first alternating current applied to the wireless power transmitter unit 610. That is, when the distance between the coil 621 of the wireless power receiver unit 620 and the coil 611 of the wireless power transmitter unit 610 is short and the two coils are concentric, the wireless power receiver unit 620 may generate a current with high efficiency. Thus, a voltage 641 corresponding to the alternating current output from the wireless power receiver unit 620 may have little loss. Also, when the voltage 641 is input to a second rectifier, the second rectifier may transmit a second DC voltage 642 to a charger.

When there is no movement in the body, since a piezoelectric effect may be hardly generated, a voltage 651 output from the piezoelectric sensor unit 630 may be small. Accordingly, an output voltage 652 of a first rectifier may be low. Thus, a charger output voltage 660 may be similar to the sum of the output voltage 642 of the second rectifier connected to the wireless power receiver unit 620 and the output voltage 652 of the first rectifier connected to the piezoelectric sensor unit 630, and the influence of the voltage generated by the wireless power receiver unit 620 may be great.

Figure 7A:
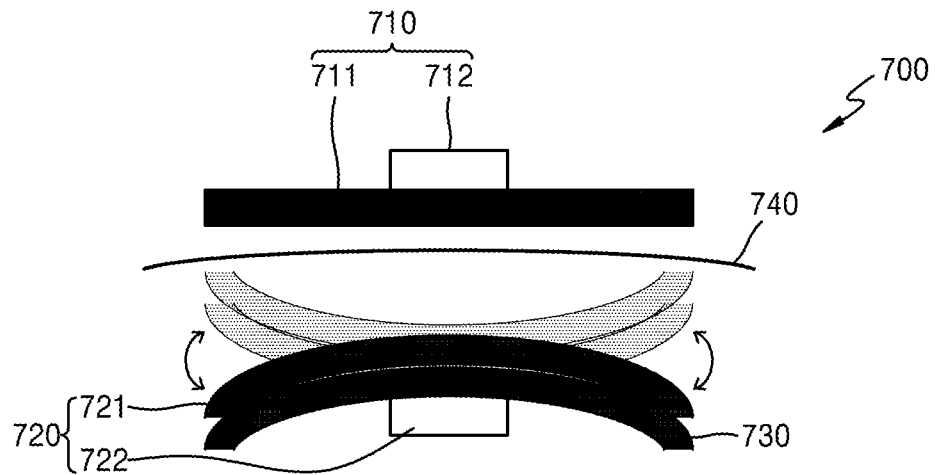
FIG. 7A is a diagram illustrating a power supply system according to an embodiment when there is a movement in a body.
Figure 7B:
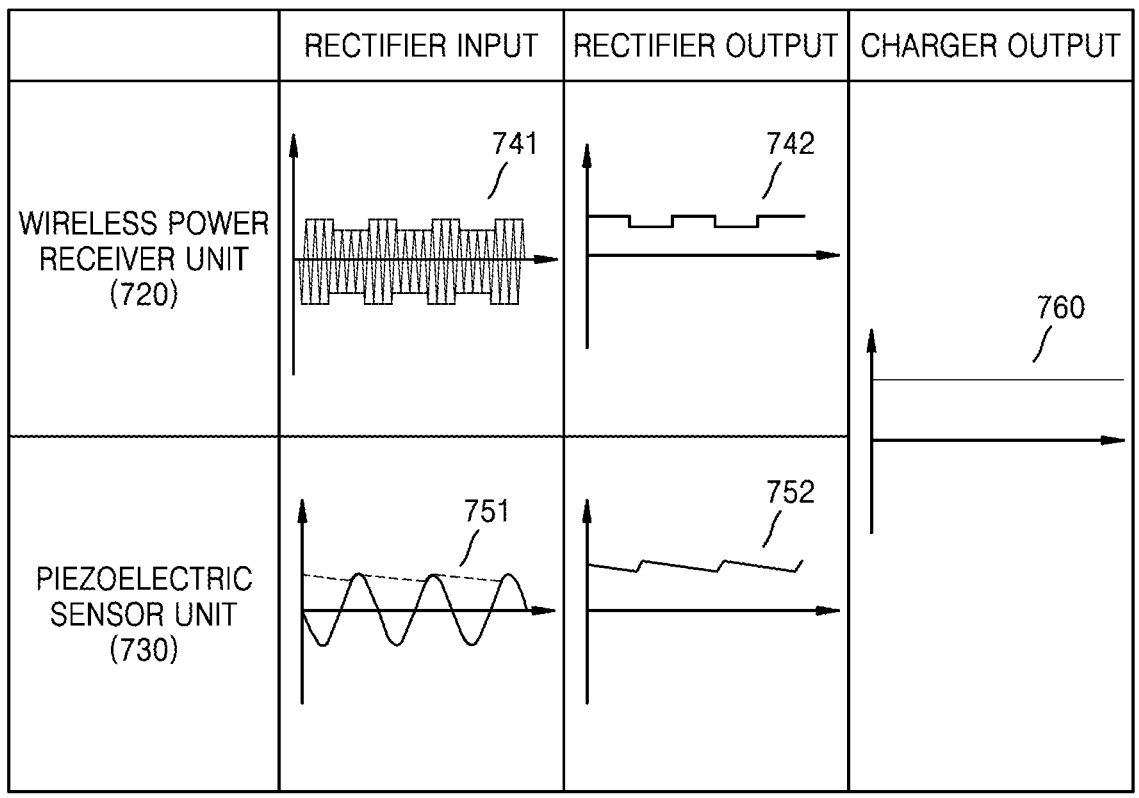
FIG. 7B is graphs illustrating voltages generated by a wireless power receiver unit and a piezoelectric sensor unit of a power supply system according to an embodiment when there is a movement in a body.

FIGS. 7A and 7B are diagrams illustrating voltages generated by a wireless power receiver unit and a piezoelectric sensor unit of a power supply system according to an embodiment when there is a movement in a body.

FIG. 7A is a diagram illustrating a power supply system according to an embodiment when there is a movement in a body.

Referring to FIG. 7A, since the material of a piezoelectric sensor unit 730 and a coil 721 of a wireless power receiver unit 720 is flexible, when there is a movement in the body, the form of the piezoelectric sensor unit 730 and the coil 721 of the wireless power receiver unit 720 may be modified. Also, the piezoelectric sensor unit 730 and the coil 721 of the wireless power receiver unit 720 fixed by a magnet 722 inside a skin 740 may be bent. In this case, since the distance between a coil 711 of a wireless power transmitter unit 710 and the coil 721 of the wireless power receiver unit 720 may increase and the coils may become eccentric, the loss of power generated by magnetic induction may increase.

FIG. 7B is graphs illustrating voltages generated by a wireless power receiver unit and a piezoelectric sensor unit of a power supply system according to an embodiment when there is a movement in a body.

Referring to FIG. 7B, it may be seen that the amplitude of a voltage 741 output from the wireless power receiver unit 720 may change according to a movement in the body. That is, in the wireless power receiver unit 720, a power loss may occur due to a movement in the body. Thus, a output voltage 742 of a second rectifier connected to the wireless power receiver unit 720 may not be constant.

Since a pressure may be applied to the piezoelectric sensor unit 730 due to a movement in the body, a voltage 751 output from the piezoelectric sensor unit 730 may be greater than the voltage 651 output from the piezoelectric sensor unit 630 of FIG. 6B. Accordingly, an output voltage 752 of a first rectifier connected to the piezoelectric sensor unit 730 may also increase.

Thus, even when the magnitude of the output voltage 742 of the second rectifier connected to the wireless power receiver unit 720 is not constant due to a movement in the body, a charger output voltage 760 substantially similar to the charger output voltage 660 of FIG. 6B may be acquired by the output voltage 752 of the first rectifier connected to the piezoelectric sensor unit 730.

Figure 8A:
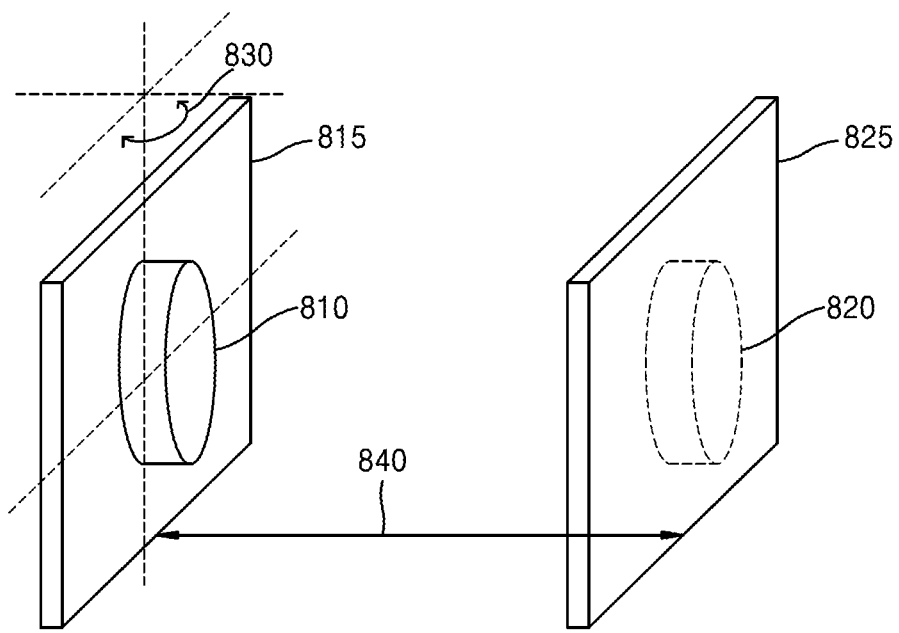
FIG. 8A is a diagram illustrating a power supply system including a wireless power transmitter unit and a wireless power receiver unit according to an embodiment when there is a movement in a body.
Figure 8B:
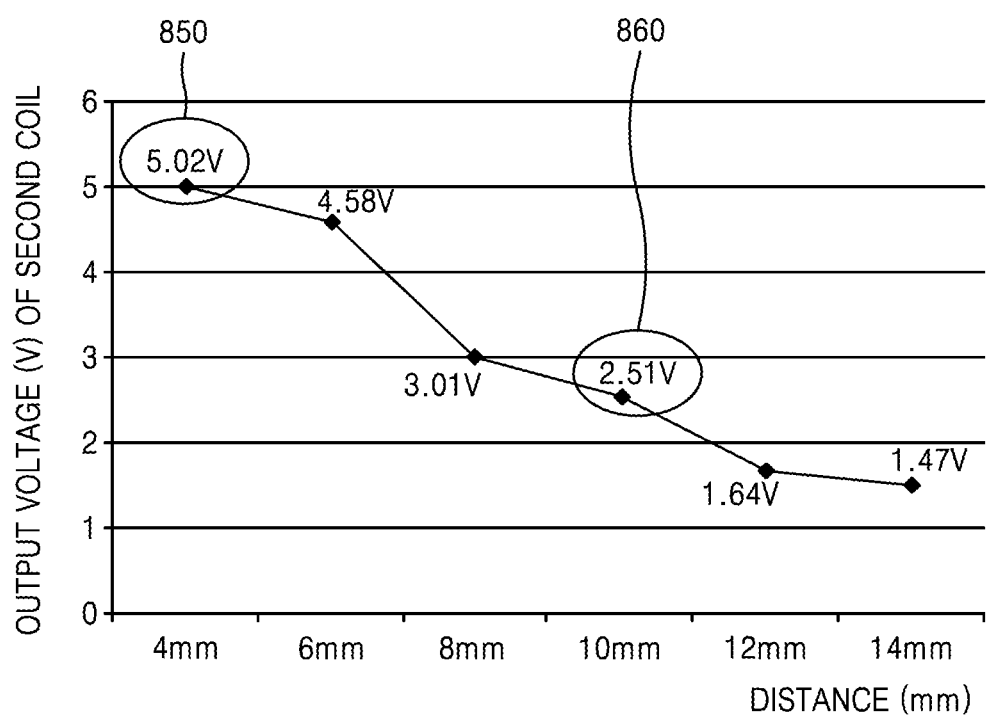
FIG. 8B is a graph illustrating a distance-dependent output voltage of a second coil according to an embodiment.
Figure 8C:
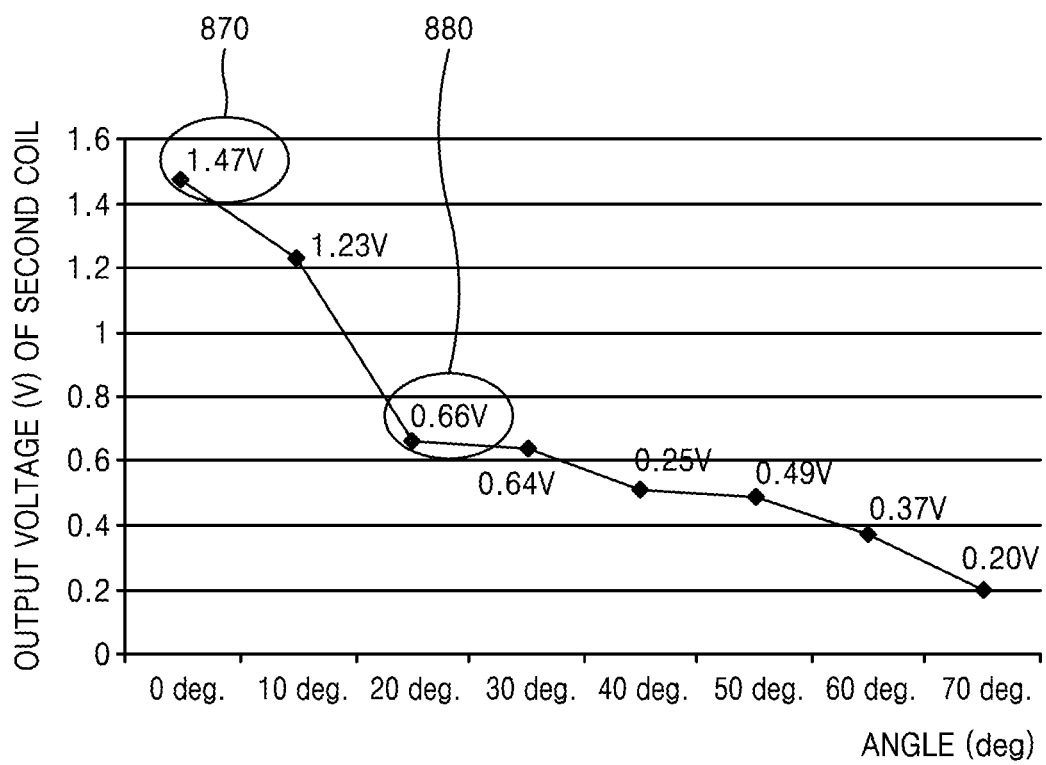
FIG. 8C is a graph illustrating an angle-dependent output voltage of a second coil according to an embodiment.

FIGS. 8A to 8C are diagrams illustrating the degree of a voltage drop in a wireless power receiver unit according to an embodiment when there is a movement in a body.

FIG. 8A is a diagram illustrating a power supply system including a wireless power transmitter unit and a wireless power receiver unit according to an embodiment when there is a movement in a body.

Referring to FIG. 8A, a first coil 810 and a second coil 820 respectively represent a coil of a wireless power transmitter unit and a coil of a wireless power receiver unit. Also, the first coil 810 and the second coil 820 are fixed respectively by a board 815 and a board 825. In this case, when power is supplied according to the magnetic induction principle, the efficiency of power generated may vary greatly according to a distance 840 between the coils and an angle 830 between the coils.

FIG. 8B is a graph illustrating a distance-dependent output voltage of a second coil according to an embodiment.

Referring to FIG. 8B, it may be seen that an output voltage of the second coil 820 may decrease as the distance between the first coil 810 and the second coil 820 increases. Specifically, when the distance between the first coil 810 and the second coil 820 increases from about 4 mm to about 10 mm, the output voltage of the second coil 820 may decrease from about 5.02 V (850) to about 2.51 V (860). That is, it may be seen that the power transmission efficiency may decrease by about 50% when the distance increases by about 6 mm from about 4 mm. Thus, when the power supply system generates power based on the magnetic induction principle, the output voltage of the coil of the wireless power receiver unit may decrease greatly as the distance between the wireless power transmitter unit and the wireless power receiver unit increases.

FIG. 8C is a graph illustrating an angle-dependent output voltage of a second coil according to an embodiment.

Referring to FIG. 8C, it may be seen that the output voltage of the second coil 820 may decrease as the angle between the first coil 810 and the second coil 820 increases. Specifically, when the angle between the first coil 810 and the second coil 820 increases from about 0 degree to about 20 degrees, the output voltage of the second coil 820 may decrease from about 1.47V (870) to about 0.66V (880). That is, it may be seen that the power transmission efficiency may decrease by about 44% when the angle increases by about 20 degrees from about 0 degree. Thus, it may be seen that the output voltage of the coil of the wireless power receiver unit may decrease greatly as the angle of the wireless power transmitter unit and the wireless power receiver unit of the power supply system increases.

Referring to FIGS. 8B and 8C in combination, in the case of the wireless power generated by the wireless power receiver unit, when the form of the wireless power transmitter unit is modified due to a movement in the body and thus the angle or distance from the wireless power transmitter unit increases, the power loss may increase. In this case, the power supply system may hardly supply a constant power to the implantable medical device.

Figure 9A:
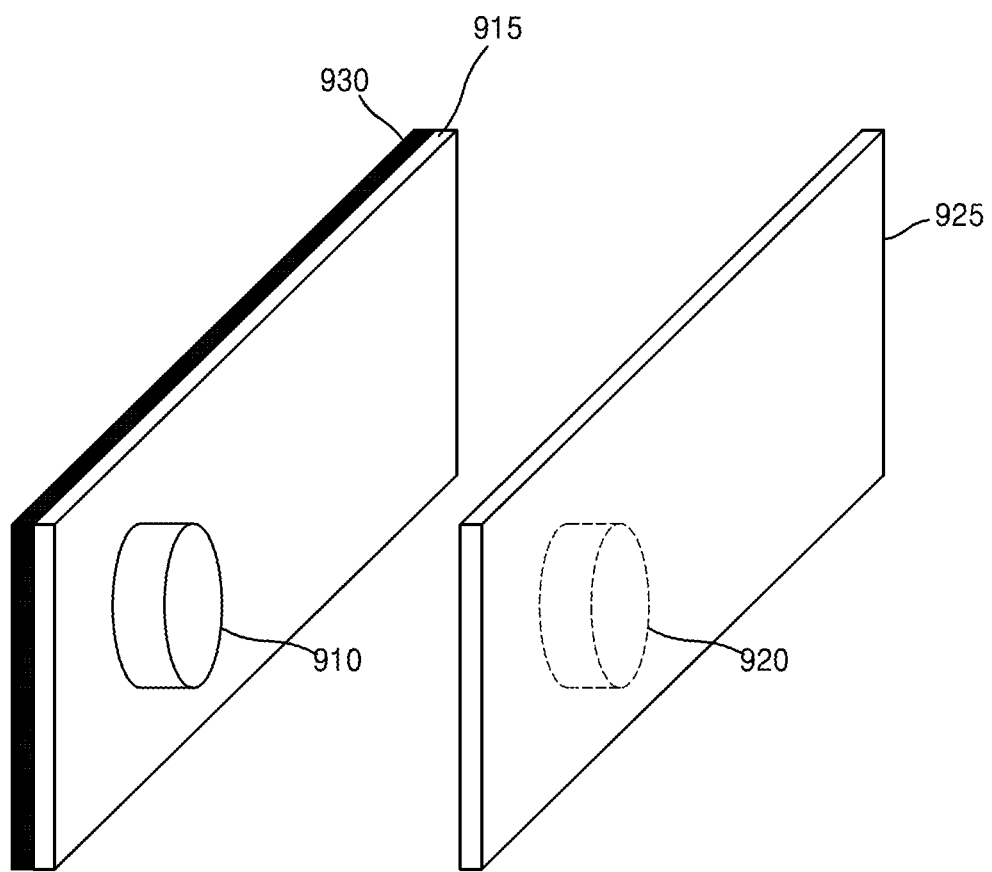
FIG. 9A is a diagram illustrating a power supply system including a wireless power transmitter unit, a wireless power receiver unit, and a piezoelectric sensor unit according to an embodiment when there is a movement in a body.
Figure 9B:
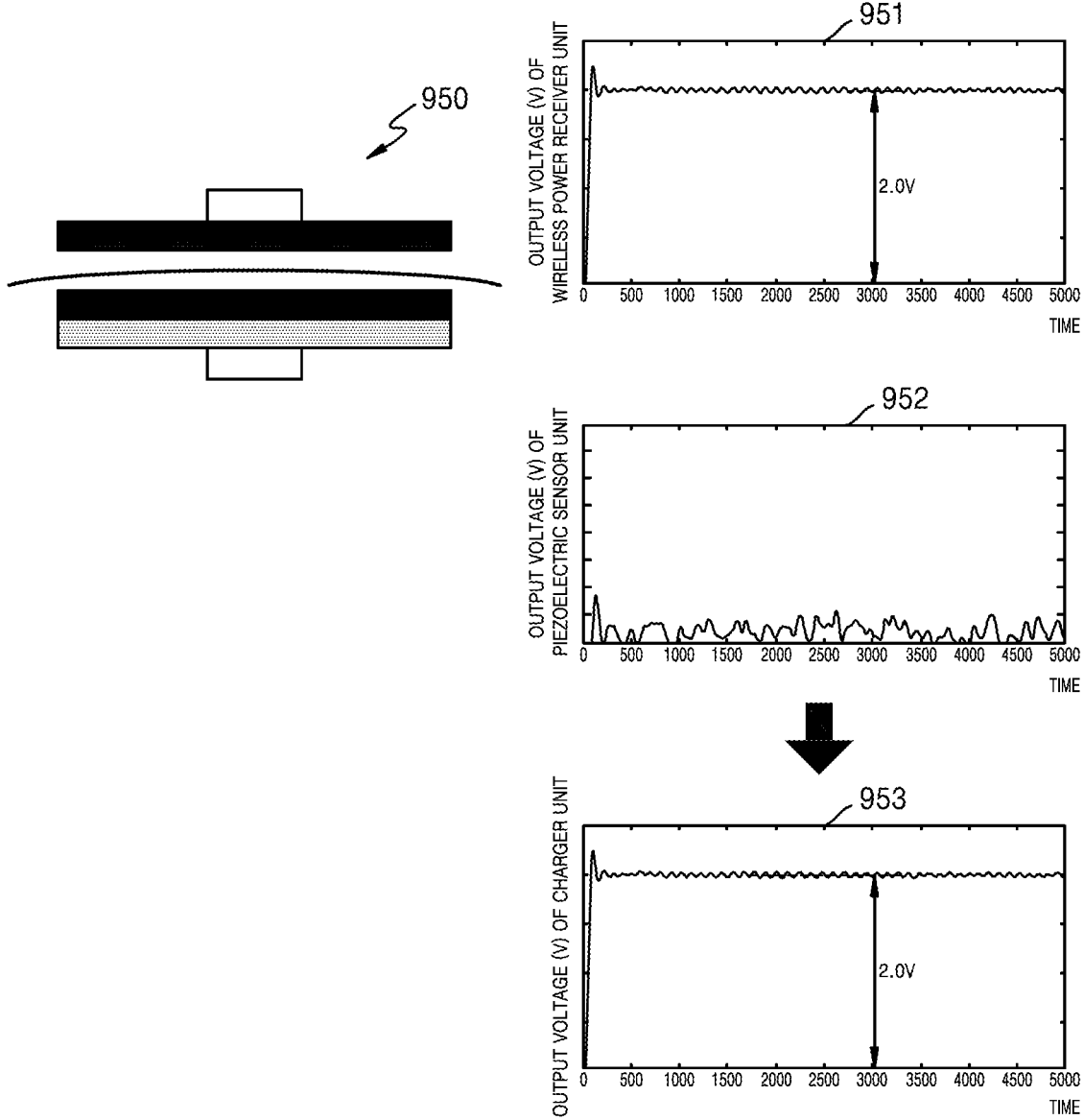
FIG. 9B is graphs illustrating voltages generated by a power supply system according to an embodiment when there is no movement in a body.
Figure 9C:
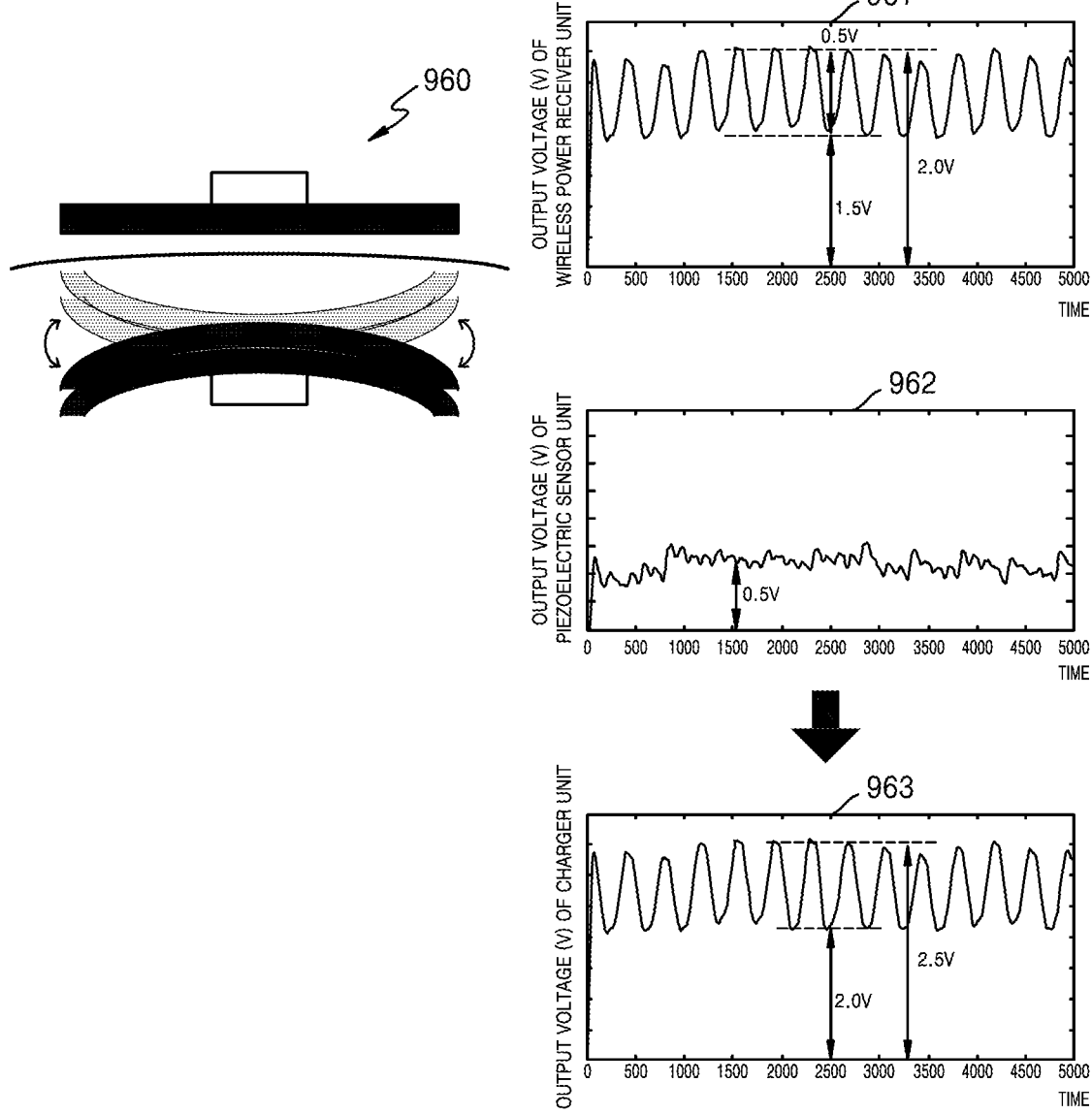
FIG. 9C is graphs illustrating voltages generated by a power supply system according to an embodiment when there is a movement in a body.

FIGS. 9A to 9C are diagrams illustrating voltages generated by a wireless power receiver unit and a piezoelectric sensor unit according to an embodiment when there is a movement in a body.

FIG. 9A is a diagram illustrating a power supply system including a wireless power transmitter unit, a wireless power receiver unit, and a piezoelectric sensor unit according to an embodiment when there is a movement in a body.

Referring to FIG. 9A, a first coil 910 and a second coil 920 respectively represent a coil of a wireless power transmitter unit and a coil of a wireless power receiver unit. Also, the first coil 910 and the second coil 920 are fixed respectively by a board 915 and a board 925. Also, a piezoelectric sensor 930 may be stacked at the board 915 fixing the first coil 910. The piezoelectric sensor 930 may represent the piezoelectric sensor unit of the power supply system.

In this case, the form of the piezoelectric sensor 930 may be modified when the board 915 fixing the first coil 910 is moved by the pressure applied from the outside. In this case, the piezoelectric sensor 930 may generate a voltage.

That is, FIG. 9A illustrates the configuration of an experiment for detecting how the voltage generated by the piezoelectric sensor unit and the coil of the wireless power receiver unit included in the power supply system varies when there is a movement in the body.

FIG. 9B is graphs illustrating voltages generated by a power supply system according to an embodiment when there is no movement in a body.

A power supply system 950 of FIG. 9B has the same configuration as the power supply system 600 of FIG. 6A, and thus detailed descriptions thereof will be omitted herein.

When there is no movement in the body, the wireless power receiver unit may receive wireless power with high efficiency from the wireless power transmitter unit. Thus, an output voltage 951 of the wireless power receiver unit may maintain a substantially constant value. On the other hand, when there is no movement, since a piezoelectric effect is hardly expected, an output voltage 952 of the piezoelectric sensor unit is similar to about 0 V.

In this case, an output voltage 953 of the charger unit may be defined as the sum of the output voltage 951 of the wireless power receiver unit and the output voltage 952 of the piezoelectric sensor unit. Thus, since the output voltage 952 of the piezoelectric sensor unit is similar to about 0 V, the output voltage 953 of the charger unit may be similar to the output voltage 951 of the wireless power receiver unit.

FIG. 9C is graphs illustrating voltages generated by a power supply system according to an embodiment when there is a movement in a body.

A power supply system 960 of FIG. 9C has the same configuration as the power supply system 700 of FIG. 7A, and thus detailed descriptions thereof will be omitted herein.

When there is a movement in the body, since the angle and distance between the wireless power receiver unit and the wireless power transmitter unit may change, the power generated by the magnetic induction principle may decrease. Thus, the amplitude of an output voltage 961 of the wireless power receiver unit may increase. Since the form of the piezoelectric sensor unit may be modified due to a movement in the body, a voltage may be generated by the piezoelectric effect. Thus, an output voltage 962 of the piezoelectric sensor unit may vary with time but may maintain a substantially constant value.

In this case, since an output voltage 963 of the charger unit may be equal to the sum of the output voltage 961 of the wireless power receiver unit and the output voltage 962 of the piezoelectric sensor unit, the output voltage 963 of the charger unit may have a great amplitude but may maintain a substantially constant value.

That is, the output voltage 963 of the charger unit of FIG. 9C may have a greater amplitude than the output voltage 953 of the charger unit of FIG. 9B, but may maintain substantially the same value as the output voltage 953 of the charger unit of FIG. 9B. Thus, even when the power loss generated in the wireless power receiver unit due to a movement in the body is great, the power supply system may supply a constant power to the implantable medical device by the voltage generated by the piezoelectric sensor unit.

Figure 10:
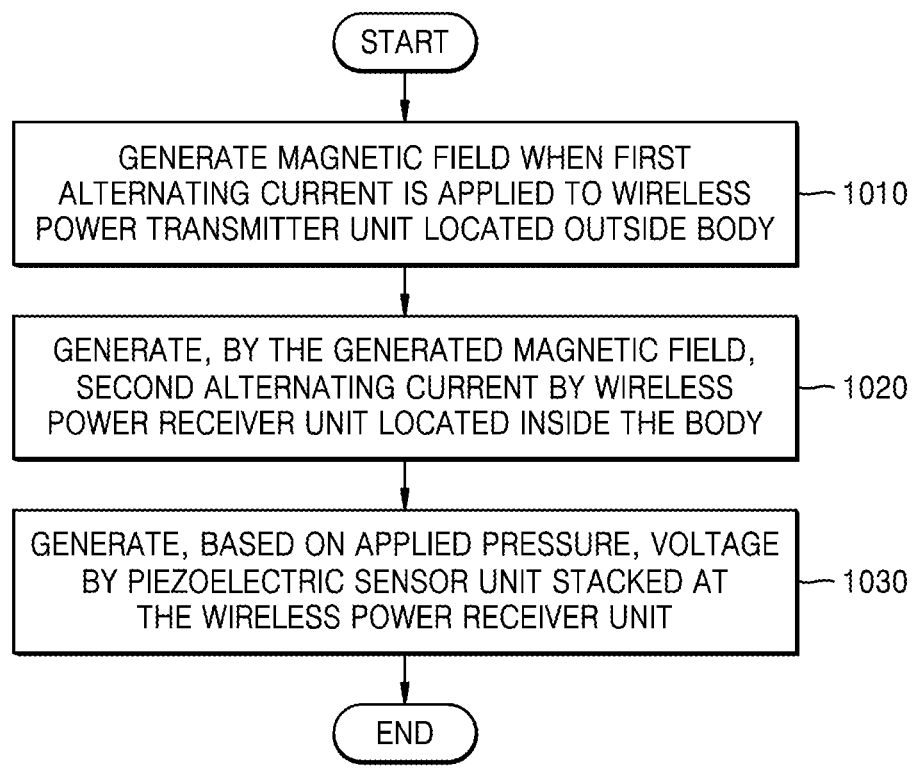
FIG. 10 is a flow diagram illustrating a method for supplying power to an implantable medical device according to an embodiment.

FIG. 10 is a flow diagram illustrating a method for supplying power to an implantable medical device according to an embodiment.

In operation 1010, a magnetic field may be generated when a first alternating current is applied to the wireless power transmitter unit 410 located outside the body.

In operation 1020, by the generated magnetic field, a second alternating current may be generated by the wireless power receiver unit 420 located inside the body. Specifically, due to the magnetic field generated by the wireless power transmitter unit 410 in operation 1010, a magnetic field may be generated in the wireless power receiver unit 420 and a second alternating current may be generated by the wireless power receiver unit 420. In this case, the magnitude of the second alternating current generated by the wireless power receiver unit 420 may decrease as the angle and/or distance between the wireless power transmitter unit 410 and the wireless power receiver unit 420 increases. Thus, when there is a movement in the body, the magnitude of the second alternating current generated by the wireless power receiver unit 420 may decrease.

In operation 1030, based on an applied pressure, a voltage may be generated by the piezoelectric sensor unit 430 stacked at the wireless power receiver unit 420. The piezoelectric sensor unit 430 may generate a voltage due to the piezoelectric effect, and it may compensate for the power when the magnitude of the wireless power generated by the wireless power receiver unit 420 due to a movement in the body decreases.

In this case, the second alternating current may be shielded by the shield unit 450.

Also, the power supply system 400 may charge the voltage generated by the wireless power receiver unit 420 and the voltage generated by the piezoelectric sensor unit 430. In this case, the charging of the voltage may include: converting the voltage output from the piezoelectric sensor unit 430 into a first DC voltage; converting a second AC voltage corresponding to the second alternating current output from the wireless power receiver unit 420 into a second DC voltage; and charging the first DC voltage and the second DC voltage.

Also, the power supply system 400 may supply a constant power to the implantable medical device 460 by using the charged voltage.

The scope of the present embodiments is defined not by the above detailed descriptions but by the following claims, and all modifications or differences within the scope of the claims should be construed as being included in the present disclosure.

The invention claimed is:

1. A power supply system for an implantable medical device, the power supply system comprising:
    a wireless power transmitter unit located outside a body and configured to generate a magnetic field in response to a first alternating current (AC) being applied thereto;
    a wireless power receiver unit located inside the body and configured to generate a second alternating current in response to the magnetic field generated by the wireless power transmitter unit;
    a piezoelectric sensor unit stacked at the wireless power receiver unit and configured to generate a voltage in response to a pressure applied thereto;
    a charger unit configured to transmit power based on a voltage corresponding to the generated second alternating current received from the wireless power receiver unit and the generated voltage received from the piezoelectric sensor unit; and
    a shield unit located between the wireless power receiver unit and the piezoelectric sensor unit and configured to shield the second alternating current.

2. The power supply system of claim 1, wherein the wireless power receiver unit and the piezoelectric sensor unit have a flexible form.

3. The power supply system of claim 2, wherein
    the form of the piezoelectric sensor unit stacked at the wireless power receiver unit is configured to be modified in response to the form of the wireless power receiver unit being modified due to a pressure applied thereto as the body moves; and the piezoelectric sensor unit is configured to generate a voltage in response to the modification.

4. The power supply system of claim 1, wherein the wireless power receiver unit comprises:
   a coil configured to generate the second alternating current; and
   a magnet configured to fix the coil.

5. The power supply system of claim 4, wherein the piezoelectric sensor unit is located between the coil and the magnet.

6. The power supply system of claim 1, wherein the charger unit is configured to charge a voltage output from the wireless power receiver unit and a voltage output from the piezoelectric sensor unit.

7. The power supply system of claim 6, wherein the charger unit comprises:
   a first rectifier configured to convert a voltage output from the piezoelectric sensor unit into a first direct current (DC) voltage;
   a second rectifier configured to convert the voltage corresponding to the second alternating current output from the wireless power receiver unit into a second DC voltage; and
   a charger configured to transmit a DC voltage based on the first DC voltage and the second DC voltage.

8. The power supply system of claim 6, wherein the charger unit is configured to transmit the power as a constant power to the implantable medical device.

9. The power supply system of claim 1, wherein the wireless power receiver unit is located at a subcutaneous fat of the body.

10. A method for supplying power to an implantable medical device, the method comprising:
    generating a magnetic field in response to a first alternating current (AC) being applied to a wireless power transmitter unit located outside a body;
    generating a second alternating current in response to the generated magnetic field by a wireless power receiver unit located inside the body;
    generating a voltage in response to an applied pressure by a piezoelectric sensor unit stacked at the wireless power receiver unit; and
    transmitting power, by a charger unit, based on a voltage corresponding to the generated second alternating current received from the wireless power receiver unit and the generated voltage received from the piezoelectric sensor unit,
    wherein a shield unit is located between the wireless power receiver unit and the piezoelectric sensor unit, and the method further comprises shielding, using the shield unit, the generated second alternating current.

11. The method of claim 10, wherein the wireless power receiver unit and the piezoelectric sensor unit have a flexible form.

12. The method of claim 11, wherein
    the form of the piezoelectric sensor unit stacked at the wireless power receiver unit is configured to be modified in response to the form of the wireless power receiver unit being modified due to a pressure applied thereto as the body moves; and
    the piezoelectric sensor unit is configured to generate a voltage in response to the modification.

13. The method of claim 10, wherein the wireless power receiver unit comprises:
    a coil configured to generate the second alternating current; and
    a magnet configured to fix the coil.

14. The method of claim 13, wherein the piezoelectric sensor unit is located between the coil and the magnet.

15. The method of claim 10, further comprising charging a voltage output from the wireless power receiver unit and a voltage output from the piezoelectric sensor unit.

16. The method of claim 15, wherein the charging comprises:
    converting a voltage output from the piezoelectric sensor unit into a first direct current (DC) voltage;
    converting the voltage corresponding to the second alternating current output from the wireless power receiver unit into a second DC voltage; and
    transmitting a DC voltage based on the first DC voltage and the second DC voltage.

17. The method of claim 15, the transmitting of the power comprises transmitting a constant power to the implantable medical device by using the charged voltage.

18. The method of claim 10, wherein the wireless power receiver unit is located at a subcutaneous fat of the body.

* * * * *